(12) United States Patent
Ehlers et al.

(10) Patent No.: US 9,848,770 B2
(45) Date of Patent: Dec. 26, 2017

(54) MICROSCOPE-INTEGRATED OCT SYSTEM WITH AN ELECTRICALLY TUNABLE FOCUS

(71) Applicant: THE CLEVELAND CLINIC FOUNDATION, Cleveland, OH (US)

(72) Inventors: Justis P. Ehlers, Shaker Hts., OH (US); Yuankai K. Tao, Cleveland, OH (US); Sunil K. Srivastava, Shaker Hts., OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 213 days.

(21) Appl. No.: 14/466,628

(22) Filed: Aug. 22, 2014

(65) Prior Publication Data

US 2015/0055093 A1     Feb. 26, 2015

Related U.S. Application Data

(60) Provisional application No. 61/868,645, filed on Aug. 22, 2013.

(51) Int. Cl.
*A61B 3/14* (2006.01)
*A61B 3/10* (2006.01)
*A61B 3/13* (2006.01)

(52) U.S. Cl.
CPC ............... *A61B 3/102* (2013.01); *A61B 3/13* (2013.01); *A61B 3/14* (2013.01)

(58) Field of Classification Search
CPC .................................. A61B 3/102; A61B 3/13
USPC ....................................................... 351/206
See application file for complete search history.

(56) References Cited

U.S. PATENT DOCUMENTS

| 5,537,162 A | 7/1996 | Hellmuth et al. |
| 8,366,271 B2 | 2/2013 | Izatt et al. |
| 2012/0140173 A1 | 6/2012 | Uhlhorn et al. |
| 2013/0169971 A1 | 7/2013 | Brown et al. |

FOREIGN PATENT DOCUMENTS

WO     2013151879 A1     10/2013

OTHER PUBLICATIONS

Ehlers et al. "Contrast-enhanced intraoperative optical coherence tomography." British Journal of Ophthalmology 97.11 (2013): 1384-1386.
Ehlers et al. "Intrasurgical dynamics of macular hole surgery: an assessment of surgery-induced ultrastructural alterations with intraoperative optical coherence tomography." Retina 34.2 (2014): 213-221.
Ehlers et al. "Novel microarchitectural dynamics in rhegmatogenous retinal detachments identified with intraoperative optical coherence tomography." Retina 33.7 (2013): 1428-1434.
Ehlers et al. "Visualisation of contrast-enhanced intraoperative optical coherence tomography with indocyanine green." British Journal of Ophthalmology 98.11 (2014): 1588-1591.

(Continued)

*Primary Examiner* — Jack Dinh
(74) *Attorney, Agent, or Firm* — Tarolli, Sundheim, Covell & Tummino LLP

(57) ABSTRACT

A surgical imaging system is provided. The surgical imaging system includes a surgical microscope and a telecentric optical coherence tomography scanning unit configured to scan a sample through at least one optical component associated with the surgical microscope.

15 Claims, 2 Drawing Sheets

(56) References Cited

OTHER PUBLICATIONS

Ehlers et al. "Analysis of Pars Plana Vitrectomy for Optic Pit-Related Maculopathy With Intraoperative Optical Coherence Tomography: A Possible Connection With the Vitreous Cavity." Archives of ophthalmology 129.11 (2011): 1483-1486.
Ehlers et al. "Visualization of real-time intraoperative maneuvers with a microscope-mounted spectral domain optical coherence tomography system." Retina (Philadelphia, Pa.) 33.1 (2013): 232.
Joos et al. "Miniature real-time intraoperative forward-imaging optical coherence tomography probe." Biomedical optics express 4.8 (2013): 1342-1350.
Klein et al. "Joint aperture detection for speckle reduction and increased collection efficiency in ophthalmic MHz OCT." Biomedical optics express 4.4 (2013): 619-634.
Nassif et al. "In vivo high-resolution video-rate spectral-domain optical coherence tomography of the human retina and optic nerve." Optics Express 12.3 (2004): 367-376.
Song et al. "Fiber-optic OCT sensor guided "SMART" microforceps for microsurgery." Biomedical optics express 4.7 (2013): 1045-1050.
Tao et al. "Intraoperative spectral domain optical coherence tomography for vitreoretinal surgery." Optics letters 35.20 (2010): 3315-3317.
Wojtkowski et al. "Ultrahigh-resolution, high-speed, Fourier domain optical coherence tomography and methods for dispersion compensation." Optics express 12.11 (2004): 2404-2422.
Xu et al. "Automated Volumetric Analysis of Interface Fluid in Descemet Stripping Automated Endothelial Keratoplasty Intraoperative Using Optical Coherence Tomography." Investigative ophthalmology & visual science 55.9 (2014): 5610.
International Search Report and Written Opinion for PCT/US2014/052352, dated Apr. 8, 2015, pp. 1-14.

MICROSCOPE-INTEGRATED OCT SYSTEM WITH AN ELECTRICALLY TUNABLE FOCUS

RELATED APPLICATIONS

This application claims priority to U.S. Provisional Patent Application Ser. No. 61/868,645 filed Aug. 22, 2013, the entire content of which is hereby incorporated by reference.

BACKGROUND OF THE INVENTION

Field of the Invention

The invention relates generally to medical imaging technologies. More specifically, the invention relates to a microscope-integrated optical coherence tomography system with an electrically tunable focus.

Background of the Invention

Over the years, multiple milestones have revolutionized ophthalmic surgery. X-Y surgical microscope control, wide-angle viewing, and fiber optic illumination are all examples of instrumentation that have been integrated to radically improve pars plana ophthalmic surgery. A major advance in ophthalmic surgery may be the integration of retinal imaging into the operating room. Optical coherence tomography (OCT) has dramatically increased the efficacy of treatment of ophthalmic disease through improvement in diagnosis, understanding of pathophysiology, and monitoring of progression over time. Its ability to provide a high-resolution, cross-sectional, three-dimensional view of the relationships of ophthalmic anatomy during surgery makes intraoperative OCT a logical complement to the ophthalmic surgeon.

SUMMARY OF THE INVENTION

In accordance with an aspect of the present invention, a surgical imaging system is provided. The surgical imaging system includes a surgical microscope and a telecentric optical coherence tomography (OCT) scanning unit configured to scan a sample through at least one optical component associated with the surgical microscope.

BRIEF DESCRIPTION OF THE DRAWINGS

The features, objects, and advantages of the invention will become more apparent from the detailed description set forth below when taken in conjunction with the drawings, wherein.

DETAILED DESCRIPTION OF THE INVENTION

Figure 1:
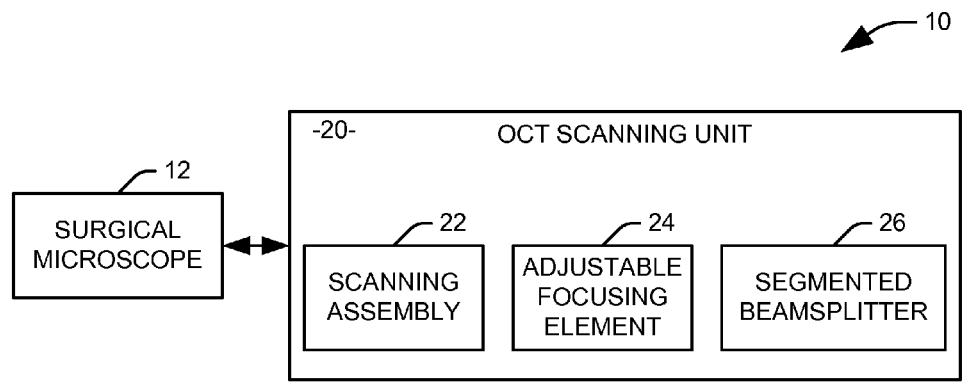
FIG. 1 illustrates one example of a microscope-integrated OCT system in accordance with an aspect of the present invention.

Optical coherence tomography (OCT) has become the gold standard for disease diagnostics and tracking therapeutic response in ophthalmology. Current-generation ophthalmic OCT systems provide high-resolution images of tissue layers in both the anterior and posterior segment that are poorly visualized with other conventional imaging modalities. Preoperative and perioperative OCT imaging, using tabletop or microscope-coupled OCT systems, respectively, provide volumetric data sets of pathologic areas and are used for clinical decision-making and surgical planning. Intraoperative OCT would provide real-time visualization of tissue microstructure deformation, feedback on surgical maneuvers, and confirm completion of surgical goals.

The utility of intraoperative OCT has been demonstrated in clinical studies using perioperative imaging during ophthalmic surgical procedures. These studies include visualization of epiretinal membranes, macular holes, retinal detachments, vitreomacular traction, and lamellar keratoplasty. These studies were predominantly performed using handheld or microscope-coupled (i.e., not parfocal to the surgical microscope) OCT systems. While perioperative imaging provides valuable information regarding structural changes as a result of surgical maneuvers, aiming the imaging field to identify regions-of-interest is difficult and without true surgical microscope integration, real-time surgical visualization and guidance is impossible.

While microscope-integrated OCT has ergonomic advantages over perioperative imaging, translation to the surgical suite has been limited because of a lack of commercial system availability and the bulky system design and cumbersome operation of research systems. A proposed system, as presented herein, includes optical and mechanical designs for a microscope-integrated intraoperative OCT system (iOCT), which includes an electrically tunable lens and heads-up display (HUD) for real-time intraoperative feedback. The system also allows for visualization methods to facilitate integration of iOCT volumetric data into the surgical field and imaging of surgical maneuvers, allowing for real-time image-guided surgery.

The present invention provides novel optical and mechanical designs for a microscope-integrated intraoperative optical coherence tomography system with enhanced function and ergonomics for visualization of ophthalmic surgical maneuvers. Integration of an electrically tunable lens allows rapid focal plane adjustment and iOCT imaging of both anterior and posterior segment tissue microstructures while maintaining parfocality with the ophthalmic surgical microscope. The invention further provides for visualization of instrument positions relative to tissue layers of interest as colormap overlays onto en face OCT data, which may provide integrative display of volumetric information during surgical maneuvers. Finally, the system provides a heads-up display system to provide real-time feedback for iOCT-guided ophthalmic surgery.

FIG. 1 illustrates one example of a microscope-integrated OCT system 10 in accordance with an aspect of the present invention. The system 10 includes a surgical microscope 12, and an OCT scanning unit 20 configured to image a target location in conjunction with at least one optical component associated with the surgical microscope 12, such as an objective lens. In accordance with an aspect of the invention, the OCT scanning unit 20 is designed to be fully telecentric, allowing the OCT scanning unit 20 to adapt in changes in the optical power of one or more optical elements of the surgical microscope, such as an objective lens.

Current generation tabletop and microscope-integrated OCT systems utilize actuating mirrors for two-dimensional lateral scanning of their imaging beam. In combination with the axial sectioning capabilities of OCT, this yields three-dimensional tomograms of the tissues of interest. These actuating mirrors are generally paired galvanometer scanners, but may consist of resonant scanners and MEMS scanners or a combination thereof. To reduce system complexity, conventional OCT systems position paired scanners in close proximity, but do not optically image the angular scan fields between the mirror faces to the back aperture of their imaging objective or pupil plane.

The telecentricity of the scanning assembly 20 can be accomplished via multiple means. In one implementation, a scanning assembly 22 of the OCT scanning unit uses, in addition to two scanning mirrors, two reflective components, such as curved (e.g., spherical, parabolic, and conical) or segmented mirrors. Each scanning mirror can be implemented to be electrically rotated such that a position of a light beam from the OCT scanning unit or an associated OCT engine (not shown), can be altered in an associated axis of the imaging plane. Alternatively, a single two-dimensional scanning mirror with its scan pivot imaged using a single imaging relay, such as a curved or segmented mirror, may also be used to maintain telecentricity. Accordingly, the OCT scanning unit 20 can adapt with the optical component associated with the surgical microscope 12.

One consequence of these non-telecentric scanning systems is a slightly curved imaging plane that may be concave, convex, or a combination of the two for x and y scanning dimensions, depending on the position of the scan lens. Similarly, the lateral extent in the x or y dimensions are also affected by the relative position of the scan lens in these systems. However, these image artifacts are not readily noticeable on conventional OCT systems because the scan lens is positioned to optically relay a point between the x and y scanners to the objective back aperture or pupil plane, and small curvature artifacts are not noticeable when imaging inherently curved surfaces such as the anterior or posterior segment of the eye. The inventors have determine that, in surgical-microscope integrated OCT systems, telecentricity becomes a critical design consideration because the optical power of the microscope can vary for different applications.

For example, in ophthalmological procedures, many surgical microscopes can be modified between anterior and posterior segment imaging with the addition of an indirect ophthalmoscope, consisting of a reduction lens and an ophthalmic lens. The role of the reduction lens is to change the optical power of the microscope objective to work within the imaging range of the ophthalmic lens that, in conjunction with the lens and cornea of the patient, relays an image of the posterior segment. In the absence of the telecentricity, the change in the optical power of the microscope objective by the addition of the reduction lens has severe consequences on the scan field of the OCT scanning unit 20. The OCT scanning unit is carefully designed to integrate with the objective lens power and small changes to that lens power would result in anisotropic scan dimensions in a non-telecentric design. This can be compensated for by increasing the scan angle of the affected scanner, but this has practical limitations since scanning mirror angles are generally limited to five to ten degrees of mechanical deviation. Additionally, integrated OCT systems would generally require a high magnification telescope before the surgical microscope objective to compensate for any resolution loss due to the long focal length of the objective lens, and this beam width magnification would act to further limit the angular imaging range of the OCT scanning unit 20.

In accordance with another aspect of the present invention, the OCT scanning unit 20 can further include an adjustable focusing element 24 positioned on the optical path before any scanning optics, such as the scanning mirrors 22, to mitigate changes in scan field and compensate for focal changes in real-time. The ophthalmic lens in tabletop and posterior segment surgical microscopes may be used to adjust focus, but large changes made during surgical maneuvers may result in drastic focal changes that, if compensated by moving the ophthalmic lens, may further result in scan field anisotropy. In one example, the adjustable focusing element 24 can comprise a segmented or deformable optical element that enables changing a phase of the OCT beam within the optical path to compensate for optical aberrations within the optics or sample. Alternatively, the adjustable focusing element 24 can include directly addressable positions within an electro-optic element, acousto-optic element, a liquid crystal matrix, or a transparent or semitransparent material with an adjustable refractive index. In one implementation, the adjustable focusing element 24 can include one or more of an electrowetting lens, an electrically tunable lens, and a deformable mirror. The adjustable focusing element 24 can be integrated with computational methods for image tracking to automatically adjust focus positions and track certain layers of interest. This is particularly useful in newer generation swept-sources with imaging ranges several times that of conventional systems. In these systems, layers of interest may stay within the overall imaging range of the imaging system during surgical maneuvers but will be outside of the depth of focus of the OCT unless actively tracked.

Finally, the invention can utilize a split aperture approach in which portions of the conjugate plane are directed into different optical paths and detected concurrently or separately on different OCT interferometers. The inventors have determined that the OCT scan beams can be selectively projected to the objective lens (not shown) of the surgical microscope 12 to utilize less than all the aperture associated with the object lens. Accordingly, different OCT scan beams can be provided to respective subapertures of a plurality of subapertures associated with the objective. For example, one or more beamsplitters 26 can be included within the OCT scanning unit such that each microscope subaperture is provided with a separate beam path. In one implementation, segmented beamsplitters can be provided for each microscope subaperture, providing an extended OCT beam with an effective width significantly greater than each individual beamsplitter. This allows for enhanced light collection and numerical aperture to improve light throughput and resolution. The beamsplitter segments can also be used to multiplex multiple OCT beam paths for increased speed, light delivery, or signal collection. Distinct beamsplitter paths can be used either as illumination or collection beam paths for darkfield/oblique illumination or collection to enhance contrast for particular scattering features or depths. It will be appreciated that the signals collected from beamsplitter segments can be combined optically, electronically, or computationally for reduced noise by angular compounding or incoherent summing.

There is generally a trade-off between resolution and reduction in the increase in the surgical microscope body length due to the incorporation of the OCT scanning unit 20. The OCT scan may be folded parfocally into the microscope path by the use of a dichroic mirror behind the objective lens, and the size of this mirror determines the overall increase in length. However, a reduction in beam diameter at this conjugate plane results in loss of resolution. By using multiple, smaller beamsplitters, this increase in the microscope body length can be reduced. Accordingly, the use of the split aperture approach can avoid or mitigate this trade-off, allowing for a decreased expansion of the surgical microscope without a significant loss of resolution.

Figure 2:
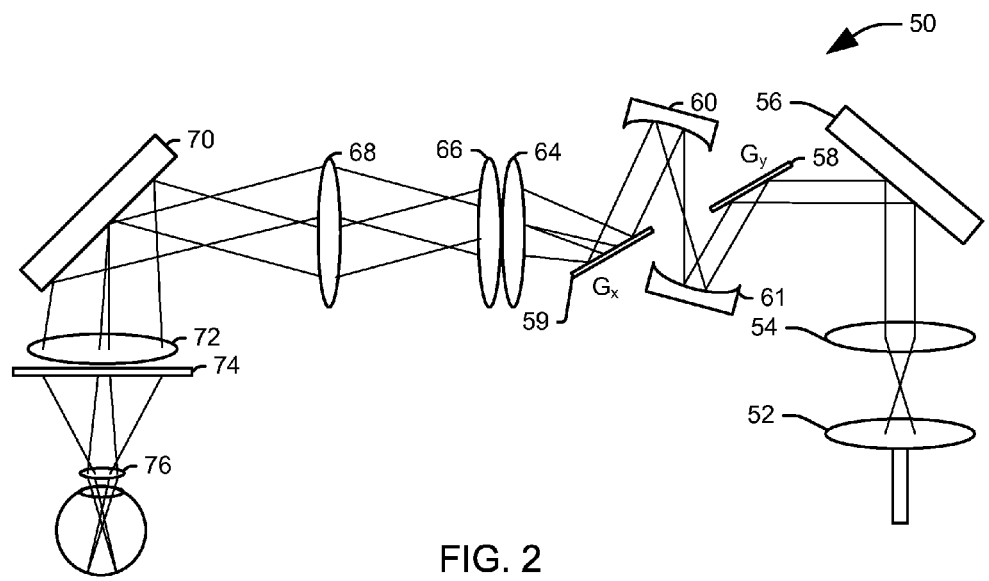
FIG. 2 illustrates one implementation of a microscope-integrated OCT system in accordance with an aspect of the present invention.

FIG. 2 illustrates one implementation of a microscope-integrated OCT system 50, referred to herein as "the iOCT system," in accordance with an aspect of the present invention. The system includes an electrically tunable lens assembly 52 configured to focus light from an associated infrared light source (not shown). It will be appreciated that the electrically tunable lens 52 can be controlled via electrical signal to alter at least one optical property of the lens, such as its optical power. This capability can allow the iOCT system 50 to adjust to changes in the optical properties of the microscope. The iOCT system 50 further includes a collimating lens 54, a fixed mirror 56, two scanning mirrors ($G_x$, $G_y$) 58 and 59, two curved mirrors 60 and 61, positioned between the scanning mirrors, a pair of scan lenses 64 and 66, a relay lens 68, and a dichroic mirror 70. In the illustrated implementation, the curved mirrors 60 and 61 are positioned in a 4-f configuration and angled and separated to reduce the effects of spherical aberration. An additional advantage to using a reflective geometry is a reduction in chromatic aberrations and better transmission efficiency.

The iOCT system can direct an OCT beam through a microscope objective 72 shared with the surgical microscope, and a BIOM retinal viewing attachment including a reduction lens 74 and an ophthalmic lens 76, for example, implemented as a non-contact wide-field lens, in order to scan the OCT beam across a field of view on target location of a patient. The backscattered OCT light may be returned back through the same optical path and re-focused by the collimating lens 54 into an optical fiber that conveys the light back to an OCT interferometer (not shown).

In practice, the system 50 is implemented as a scan-head attaches at the base of an ophthalmic surgical microscope and is mounted at the microscope nosepiece and secured by two preexisting attachment screws conventionally used to attach noncontact surgical viewing accessories (e.g., a Binocular Indirect Ophthalmo Microscope). The microscope objective is then mounted on a threaded adapter at the base of the iOCT, thus, extending the axial height of the microscope. To minimize interference with surgical ergonomics and maintain surgical field sterility, the axial height added by the iOCT was reduced via the split aperture approach described previously from the 120.5 mm associated with a standard magnetomotive OCT device to around 78.5 mm. To reduce the load on the pneumatic microscope swing arm, the body and base of the iOCT was rapid-prototyped using an ABS plastic substrate and reinforced with aluminum mounting and threaded brackets for a total of 4.32 lbs added weight. Optical mounts were designed into the iOCT body as a monolithic unit to ensure precision optical alignment and stability.

Real-time intraoperative feedback and guidance was achieved using a 1024×768 resolution heads-up display (HUD) system optically coupled into the field-of-view (FOV) of one microscope ocular using a 50:50 beamsplitter cube and interfaced with the OCT acquisition computer via a VGA input. HUD opacity could be adjusted by controlling the LCD display brightness. Real-time and post-processed OCT images may be displayed across the entire field at full brightness, completely obscuring the microscope view through one ocular; at low LCD brightness as an overlay, so both the HUD and microscope view were simultaneously visible; or projected at the periphery of the ocular field, simultaneously showing OCT and microscope views while avoiding potentially distracting or misleading overlaid features.

The iOCT system was designed for both anterior and posterior segment imaging. The sample arm fiber output was collimated to a $1/e^2$ beam waist diameter of 2.64 mm ($f_{c1}$=12.19 mm). The beam is then relayed across the electrically tunable lens 52 and the collimating lens 54 ($f_{c2}$=60 mm). The electrically tunable lens 52 provides 45-120 mm of focal length tuning, allowed real-time adjustment of the OCT focal plane to maintain parfocality with the microscope view. This allows for compensation for changes between the microscope and OCT focus when switching between anterior and posterior segment imaging, for different microscope zoom positions, and for refractive power differences between surgeons.

In one implementation, three-dimensional reconstruction and display is performed in post-processing at an associated processor (not shown). While cross-sectional OCT images provide can provide precise axial positions of surgical instruments relative to tissue microstructures of interest, the surgical field shows an en face view, which makes co-registration and integration of iOCT data complex. The illustrated implementation uses a two-layer segmentation that isolates the surface of a tool and an easily recognizable tissue structure, such as the inner limiting membrane of the retina. The difference of the axial positions of each segmented layer is then overlaid on to the en face projection of the iOCT volume as a colormap to show a distance from the selected tissue structure. Co-registered colormaps between instruments and specific tissue layers of interest may be displayed as additional contrast on HUD systems to provide real-time guidance during surgical maneuvers. While real-time segmentation is computationally intensive, the inventors have determined that only cross-sectional images spanning the surgical instrument have to be segmented, and by using real-time visualization methods such as spatial compounding, only 5-10 OCT B-scans are needed to provide sufficient information. In the illustrated implementation, these B-scans can be segmented in less than half of a second.

Figure 3:
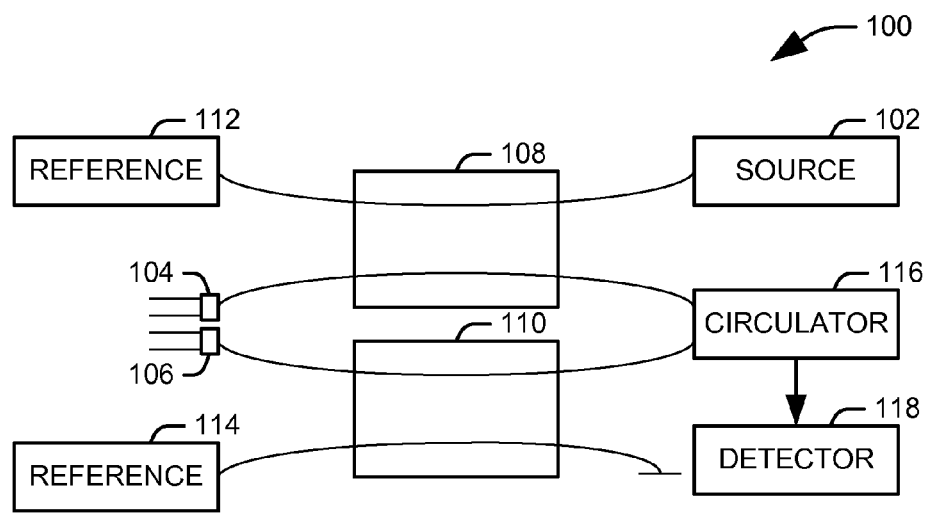
FIG. 3 illustrates a schematic diagram of one implementation of the imaging system highlighting the split aperture OCT integration.
Figure 4:
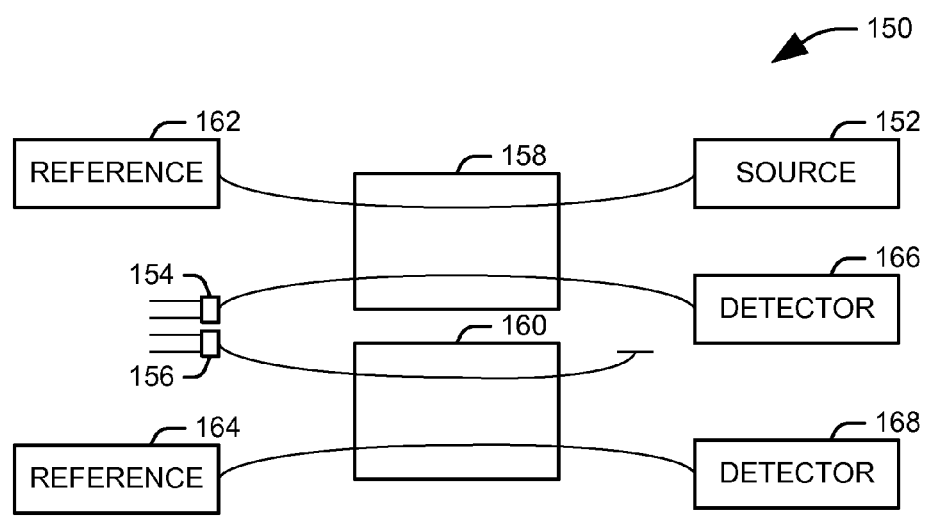
FIG. 4 illustrates a schematic diagram of another implementation of the imaging system highlighting the split aperture OCT integration.

FIGS. 3 and 4 illustrate a design for split aperture integration of an OCT system into an ophthalmic surgical microscope. In these implementations, separate segmented dichroic mirrors are positioned in front of each microscope subaperture in infinity space to relays OCT light to different spatial positions for cumulative or independent detection on single or multiple interferometers. In one implementation of this design, the illumination beam may be relayed via a single small dichroic mirror located between the subapertures of the microscope. In this implementation, spatial resolution is not sacrificed since the entire scattered field is still being collected via each subaperture dichroic that spans the entire infinity space. One advantage of this implementation is that it reduces the overall length increase in the body of the surgical microscopy because it is no longer governed by the dimensions of a single dichroic mirror spanning the entire infinity space. Another advantage of this implementation is that the collection efficiency of the system is no longer determined by a single dichroic mirror and the optical relay of a single illumination and detection path. Instead, each subaperture dichroic may relay scattered light collected across the entire numerical aperture of the microscope objective to separate interferometric and detection arms to improve the efficiency of signal collection.

FIG. 3 illustrates a schematic diagram of one implementation of the imaging system 100 highlighting the split aperture OCT integration. Light from an associated light source 102 is provided to respective subapertures, where a plurality of small, dichroic mirrors 104 and 106 direct light from an associated subaperture from a given spatial position and receive reflected light from the spatial position. The light received at each dichroic mirror 104 and 106 is provided to an associated interferometer 108 and 110, where the received light is associated with a reference signal from associated reference paths 112 and 114. The resulting interference pattern from each interferometer 108 and 110 is provided to a multiple port circulator 116. In one implementation, the circulator 116 can have one more port than the number of interferometers. The combined signal from the circulator 116 is then provided to a detector 118 for conversion into an electrical signal representing the combined detected interference.

FIG. 4 illustrates a schematic diagram of another implementation of the imaging system 150 highlighting the split aperture OCT integration. Light from an associated light source 152 is provided to respective subapertures, where a plurality of small, dichroic mirrors 154 and 156 direct light from an associated subaperture from a given spatial position and receive reflected light from the spatial position. The light received at each dichroic mirror 154 and 156 is provided to an associated interferometer 158 and 160, where the received light is associated with a reference signal from associated reference paths 162 and 164. The resulting interference pattern from each interferometer 158 and 160 is provided to respective detectors 166 and 168 for conversion into an electrical signal representing the detected interference.

The invention has been disclosed illustratively. Accordingly, the terminology employed throughout the disclosure should be read in an exemplary rather than a limiting manner. Although minor modifications of the invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

Having described the invention, we claim:

1. A surgical imaging system comprising:
a surgical microscope; and
a telecentric optical coherence tomography (OCT) scanning unit configured to scan a sample through at least one optical component associated with the surgical microscope, the telecentric OCT scanning unit comprising an electrically tunable focusing element.

2. The imaging system of claim 1, the electrically tunable focusing element comprising a segmented or deformable optical element that enables changing a phase of an OCT beam.

3. The imaging system of claim 1, the electrically tunable focusing element comprising one of an electrowetting lens, an electrically tunable lens, and a deformable mirror.

4. The imaging system of claim 1, wherein the electrically tunable focusing element is positioned on an optical path of the telecentric OCT scanning unit such that a scanning mirror associated with the telecentric OCT scanning unit is located between the electrically tunable element and the at least one optical component associated with the surgical microscope on the optical path.

5. The imaging system of claim 1, wherein the telecentric OCT scanning unit comprises a first scanning mirror and a second scanning mirror, each having an orientation adjustable to change a position of an OCT light beam within a scanning plane of the telecentric OCT scanning unit, and at least one curved mirror positioned between the first scanning mirror and the second scanning mirror on an optical path of the telecentric OCT scanning unit.

6. The imaging system of claim 1, wherein the telecentric OCT scanning unit comprises a two-dimensional scanning mirror with an associated scan pivot and a curved mirror.

7. The imaging system of claim 1, further comprising a plurality of dichroic mirrors in respective optical paths of each of the surgical microscope and the telecentric OCT scanning unit, such that an OCT light beam from the telecentric OCT scanning unit is directed onto the at least one optical component associated with the surgical microscope by the plurality of dichroic mirrors.

8. The imaging system of claim 1, wherein the surgical microscope comprises a plurality of subapertures, and the telecentric OCT scanning unit includes a segmented beamsplitter configured such that each subaperture of the surgical microscope is provided with a separate beam path from the telecentric OCT scanning unit.

9. The imaging system of claim 8, further comprising:
a plurality of interferometers configured such that reflected light associated with each of the plurality of subapertures provided to an associated one of the plurality of interferometers for comparison to an associated reference signal;
a multiport circulator configured to combine the outputs of the plurality of interferometers into a combined output; and
a detector configured to convert the combined output into an electrical signal.

10. The imaging system of claim 8, further comprising:
a plurality of interferometers configured such that reflected light associated with each of the plurality of subapertures provided to an associated one of the plurality of interferometers for comparison to an associated reference signal; and
a plurality of detectors each configured to convert the output of an associated one of the plurality of interferometers into an electrical signal.

11. The imaging system of claim 1, where at least one optical component associated with the surgical microscope comprises an objective lens.

12. A surgical imaging system comprising:
a surgical microscope comprising a plurality of subapertures; and
a telecentric optical coherence tomography (OCT) scanning unit configured to scan a sample through at least one optical component associated with the surgical microscope, the telecentric OCT scanning unit comprising an electrically tunable focusing element and a segmented beamsplitter configured such that each subaperture of the surgical microscope is provided with a separate beam path from the telecentric OCT scanning unit.

13. The imaging system of claim 12, further comprising:
a plurality of interferometers configured such that reflected light associated with each of the plurality of subapertures provided to an associated one of the plurality of interferometers for comparison to an associated reference signal;
a multiport circulator configured to combine the outputs of the plurality of interferometers into a combined output; and
a detector configured to convert the combined output into an electrical signal.

14. The imaging system of claim 12, further comprising:
a plurality of interferometers configured such that reflected light associated with each of the plurality of subapertures provided to an associated one of the plurality of interferometers for comparison to an associated reference signal; and a plurality of detectors each configured to convert the output of an associated one of the plurality of interferometers into an electrical signal.

15. A surgical imaging system comprising:

a surgical microscope; and a telecentric optical coherence tomography (OCT) scanning unit configured to scan a sample through at least one optical component associated with the surgical microscope, the telecentric OCT scanning unit comprising:

an electrically tunable focusing element;

a first scanning mirror having a first orientation adjustable to change a position of an OCT light beam within a scanning plane of the telecentric OCT scanning unit;

a second scanning mirror having a second orientation adjustable to change the position of the OCT light beam within the scanning plane of the telecentric OCT scanning unit; and at least one curved mirror positioned between the first scanning mirror and the second scanning mirror on an optical path of the telecentric OCT scanning unit.

* * * * *